(12) United States Patent
Bruno

(10) Patent No.: US 9,980,997 B1
(45) Date of Patent: May 29, 2018

(54) HIGH FLAVANOL COCOA POWDER COMPOSITION FOR IMPROVING ATHLETIC PERFORMANCE

(71) Applicant: James R. Bruno, Belle Vernon, PA (US)

(72) Inventor: James R. Bruno, Belle Vernon, PA (US)

( * ) Notice: Subject to any disclaimer, the term of this patent is extended or adjusted under 35 U.S.C. 154(b) by 117 days.

(21) Appl. No.: 15/086,489

(22) Filed: Mar. 31, 2016

Related U.S. Application Data

(60) Provisional application No. 62/141,304, filed on Apr. 1, 2015.

(51) Int. Cl.
| | |
|---|---|
| *A61K 36/00* | (2006.01) |
| *A61K 36/185* | (2006.01) |
| *A61K 9/00* | (2006.01) |
| *A23L 1/29* | (2006.01) |

(52) U.S. Cl.
CPC ............ *A61K 36/185* (2013.01); *A23L 1/296* (2013.01); *A61K 9/0053* (2013.01); *A23V 2002/00* (2013.01)

(58) Field of Classification Search
CPC .................................................... A61K 36/00
See application file for complete search history.

(56) References Cited

U.S. PATENT DOCUMENTS

| | | | |
|---|---|---|---|
| 2011/0045142 A1* | 2/2011 | Alpern ................. | A23L 1/3002 426/72 |
| 2014/0099412 A1* | 4/2014 | Ward ...................... | A23G 1/52 426/250 |

\* cited by examiner

*Primary Examiner* — Qiuwen Mi
(74) *Attorney, Agent, or Firm* — Buchanan Ingersoll & Rooney PC

(57) ABSTRACT

A composition and method of improving the overall strength in a mammal, improving fatigue recovery in a mammal, improving athletic recovery in a mammal, improving increased endurance in a mammal, and improving overall athletic performance in a mammal by administering the composition, in the form of a powder, liquid, bar, cookie, waffle, syrup, tablet or dietary supplement, to the mammal. The composition includes 1 to 21.32 grams of cocoa powder; 1 to 48 grams of protein; 0 to 193 grams of carbohydrate; and 0 to 24 grams of fat. The cocoa powder includes 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

35 Claims, 1 Drawing Sheet

Nutritional make-up of Treatment and Placebo

| | Weight in Grams | Protein | fat | carbs | Fiber | sugar | Saturated | Cholesterol | mg calcium | mg iron | mg potassium | mg sodium | IU a | IU d | Calories | Flavanol |
|---|---|---|---|---|---|---|---|---|---|---|---|---|---|---|---|---|
| Placebo profile for Treadmill and Weight Training | | | | | | | | | | | | | | | | |
| MILK | 32 | 11.52 | 0.26 | 16.64 | - | 16.32 | 0.16 | 8.00 | 399.36 | 0.13 | 535.68 | 158.08 | 695.68 | 139.20 | 114.88 | |
| COCOA | 5.34 | 0.97 | 0.70 | 3.11 | 1.59 | 0.09 | 0.41 | - | 5.93 | 0.83 | 133.98 | 1.01 | - | - | 11.75 | 53.40 |
| SUGAR | 10 | - | - | 9.98 | - | 9.98 | - | - | 0.10 | 0.01 | 0.20 | 0.10 | - | - | 38.70 | - |
| Total per serving | 47.34 | 12.49 | 0.96 | 29.73 | 1.59 | 26.39 | 0.57 | 8.00 | 405.39 | 0.96 | 669.86 | 159.19 | 695.68 | 139.20 | 165.33 | 53.40 |
| Placebo profile for Cycling | | | | | | | | | | | | | | | | |
| MILK | 16 | 5.76 | 0.13 | 8.32 | - | 8.16 | 0.08 | 4.00 | 199.68 | 0.06 | 267.84 | 79.04 | 347.84 | 69.60 | 57.44 | - |
| COCOA | 2.67 | 0.48 | 0.35 | 1.56 | 0.80 | 0.05 | 0.21 | - | 2.96 | 0.41 | 66.99 | 0.51 | - | - | 5.87 | 26.70 |
| SUGAR | 5 | - | - | 4.99 | - | 4.99 | - | - | 0.05 | 0.00 | 0.10 | 0.05 | - | - | 19.35 | - |
| Total per serving | 23.67 | 6.24 | 0.48 | 14.87 | 0.80 | 13.20 | 0.29 | 4.00 | 202.69 | 0.48 | 334.93 | 79.60 | 347.84 | 69.60 | 82.66 | 26.70 |
| Treatment profile for Treadmill and Weight Training | | | | | | | | | | | | | | | | |
| MILK | 32 | 11.52 | 0.26 | 16.64 | - | 16.32 | 0.16 | 8.00 | 399.36 | 0.13 | 535.68 | 158.08 | 695.68 | 139.20 | 114.88 | |
| COCOA | 5.34 | 1.17 | 0.75 | 2.94 | 0.80 | 0.16 | 0.43 | - | 6.71 | 2.24 | 80.63 | 1.07 | 0.91 | 1.36 | 12.82 | 400.50 |
| SUGAR | 10 | - | - | 9.98 | - | 9.98 | - | - | 0.10 | 0.01 | 0.20 | 0.10 | - | - | 38.70 | - |
| Total per serving | 47.34 | 12.69 | 1.00 | 29.56 | 0.80 | 26.46 | 0.59 | 8.00 | 406.17 | 2.38 | 616.51 | 159.25 | 696.59 | 140.56 | 166.40 | 400.50 |
| Treatment profile for Cycling | | | | | | | | | | | | | | | | |
| MILK | 16 | 5.76 | 0.13 | 8.32 | - | 8.16 | 0.08 | 4.00 | 199.68 | 0.06 | 267.84 | 79.04 | 347.84 | 69.60 | 57.44 | - |
| COCOA | 2.67 | 0.59 | 0.37 | 1.47 | 0.40 | 0.08 | 0.21 | - | 3.35 | 1.12 | 40.32 | 0.53 | 0.45 | 0.68 | 6.41 | 200.25 |
| SUGAR | 5 | - | - | 4.99 | - | 4.99 | - | - | 0.05 | 0.00 | 0.10 | 0.05 | - | - | 19.35 | - |
| Total per serving | 23.67 | 6.35 | 0.50 | 14.78 | 0.40 | 13.23 | 0.29 | 4.00 | 203.08 | 1.19 | 308.26 | 79.62 | 348.29 | 70.28 | 83.20 | 200.25 |

…

HIGH FLAVANOL COCOA POWDER COMPOSITION FOR IMPROVING ATHLETIC PERFORMANCE

CROSS-REFERENCE TO RELATED APPLICATIONS

This patent application claims the benefit of U.S. Provisional Patent Application No. 62/141,304, filed on Apr. 1, 2015, which is hereby incorporated by reference in its entirety.

FIELD OF THE INVENTION

The present invention relates to compositions, in powder or other form (e.g., liquid, bar, cookie, waffle, syrup, tablet, dietary supplement, etc.), containing high levels of cocoa flavanol antioxidants and which comprise an optimized ratio of cocoa to proteins, resulting in an increase in athletic performance. The composition is consumable before, during or after physical activity or exercise, or on a daily basis as a daily health supplement. Administration of the inventive composition results in improved athletic performance in a number of different meaningful performance criteria, as set forth in more detail below.

BACKGROUND OF THE INVENTION

Most athletes, whether professional or recreational, are driven with the goal of achieving peak, or at least an increased, performance. Along with that goal is the self-driven desire for self-improvement, athletic composition and improvement and/or minimizing of recovery time. Most recreational and professional athletes achieve these goals through prolonged exercise coupled with proper diet and supplements. This present invention relates to the composition of such a supplement.

Previous art and science has shown that cocoa flavanols have a benefit to the circulatory system. To date, current art and science surrounding cocoa and flavanols have predominately centered on the beneficial effects cocoa flavanols on cardiovascular health and the associated effects for blood pressure, cholesterol improvement and stabilizing glucose.

There is also previous art and science that cocoa powder can be used to produce drinks, energy bars and to enhance health and mental well-being. Additionally, previous art and science has shown that protein can contribute to enhanced athletic performance.

A problem may arise where an athlete, whether professional or recreational, may consume individual supplements for their individual effects without considering one supplements impact on other supplements. In some instances, one supplement may have a negative impact on one or more other supplements when they are consumed together in a dietary supplement program.

The present invention is directed toward overcoming one or more of the above-mentioned problems.

SUMMARY OF THE INVENTION

The present invention is based at least in part that the unexpected discovery that a large quantity of cocoa flavanols when consumed with a minimal amount of protein and other ingredients, provides additional benefits beyond each individual component in a synergistic manner. The inventive composition has been found to provide a synergistic increase in athletic performance, both physical as well as mental, during physical activity.

Multiple studies were conducted to test a product, formulated with high amounts of natural cocoa and cocoa flavanols combined with protein, on a numerical rating scale ("NRS") for their effects on athletic performance. A unique testing protocol was developed for running and strength training, as well as cycling. Results of the studies are set forth below.

The flavanol cocoa, when combined with a minimal amount of protein, enhances athletic performance by providing, among other things, increased energy, improved performance, decreased recovery time, increased perceived mental state on performance, and improved mental well-being during physical and/or mental stress, resulting in a positive and increased athletic achievement. Additionally, the unexpected benefits of an increase in distance traveled, improvement in endurance, increase in the time before total exhaustion, increase in nitric oxide and nitrate levels, lowered oxygen demands, improvement in effort extended, improvement in strength, improvement in fatigue recovery, reduction of recovery time, and an increase in time-to-complete-failure warrant and establish the present invention as a new, novel and innovative supplement composition.

In one embodiment, a method is provided for improving overall athletic performance in a mammal in need of or having a desire to improve their overall athletic performance. The method includes administering a preparation including: 1 to 21.32 grams of cocoa powder; 1 to 48 grams of protein; 0 to 193 grams of carbohydrate; and 0 to 24 grams of fat to the mammal, thereby resulting in said mammal having improvement in their overall athletic performance. The preparation includes a composition selected from a powder, liquid, bar, cookie, waffle, syrup, tablet or dietary supplement. In one form, the mammal is a human.

The cocoa powder can include 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

Various vitamins, minerals, flavoring agents and/or sweeteners can be added to the composition to enhance flavor. The protein may be animal based or plant based or chemically formulated.

In one form, the mammal is in need of: increasing endurance; athletic recovery; fatigue recovery; and/or improving overall strength.

In another embodiment, a method is provided for improving increased endurance in a mammal in need of or having a desire to improve their increased endurance. The method includes administering a preparation including: 1 to 21.32 grams of cocoa powder; 1 to 48 grams of protein; 0 to 193 grams of carbohydrate; and 0 to 24 grams of fat to the mammal, thereby resulting in said mammal having improvement in their increased endurance. The preparation includes a composition selected from a powder, liquid, bar, cookie, waffle, syrup, tablet or dietary supplement. In one form, the mammal is a human.

The cocoa powder can include 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

Various vitamins, minerals flavoring agents or sweeteners are added to the composition to enhance flavor. The protein may be animal based or plant based or chemically formulated.

In an additional embodiment, a method is provided for improving athletic recovery in a mammal in need of or having a desire to improve their athletic recovery. The method includes administering a preparation including: 1 to 21.32 grams of cocoa powder; 1 to 48 grams of protein; 1 to 148 grams of carbohydrate; and 1 to 24 grams of fat to the mammal, thereby resulting in said mammal having improvement in their athletic recover. The preparation includes a composition selected from a powder, liquid, bar, cookie, waffle, syrup, tablet or dietary supplement. In one form, the mammal is a human.

The cocoa powder can include 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

Various vitamins, minerals, flavoring agents or sweeteners are added to the composition to enhance flavor. The protein can be animal based or plant based or chemically formulated.

In a further embodiment, a method is provided for improving fatigue recovery in a mammal in need of or having a desire to improve their fatigue recovery. The method includes administering a preparation including: 1 to 21.32 grams of cocoa powder; 1 to 48 grams of protein; 1 to 148 grams of carbohydrate; and 1 to 24 grams of fat to the mammal, thereby resulting in said mammal having improvement in their fatigue recovery. The preparation includes a composition selected from a powder, liquid, bar, cookie, waffle, syrup, tablet or dietary supplement. In one form, the mammal is a human.

The cocoa powder can include 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

Various vitamins, minerals, flavoring agents or sweeteners are added to the composition to enhance flavor. The protein may be animal based or plant based or chemically formulated.

In yet a further embodiment, a method is provided for improving overall strength in a mammal in need of or having a desire to improve their overall strength. The method includes administering a preparation including: 1 to 21.32 grams of cocoa powder; 1 to 48 grams of protein; 1 to 148 grams of carbohydrate; and 1 to 24 grams of fat to the mammal, thereby resulting in said mammal having improvement in their overall strength. The preparation includes a composition selected from a powder, liquid, bar, cookie, waffle, syrup, tablet or dietary supplement. In one form, the mammal is a human.

The cocoa powder can include 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

Various vitamins, minerals, flavoring agents or sweeteners are added to the composition to enhance flavor. The protein can be animal based or plant based or chemically formulated.

In still a further embodiment, a composition is provided for consumption before, during and/or after physical activity for improving one or more of overall strength in a mammal, fatigue recovery in a mammal, athletic recovery in a mammal, increased endurance in a mammal, and overall athletic performance in a mammal. The composition includes: 1 to 21.32 grams of cocoa powder; 1 to 48 grams of protein; 0 to 193 grams of carbohydrate; and 0 to 24 grams of fat to the mammal. The composition may be selected from a powder, liquid, bar, cookie, waffle, syrup, tablet or dietary supplement. In one form, the mammal is a human.

The cocoa powder can include 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

Various vitamins, minerals, flavoring agents or sweeteners are added to the composition to enhance flavor. The protein may be animal based or plant based or chemically formulated.

It is an object of the present invention to provide an improved supplement composition, and method of administering the same, which results in improved overall strength in a mammal, improved fatigue recovery in a mammal, improved athletic recovery in a mammal, improved increased endurance in a mammal, and/or improved overall athletic performance in a mammal.

Further embodiments, features, aspects, objects, advantages, and possible applications of the present invention could be learned from the following description, in combination with the FIGURES, and the appended claims. For example, one further embodiment might include using only three ingredients such as, for example, powdered milk, high flavanol cocoa powder, and cane sugar to create a preparation, which would appeal to many athletes and athletic-minded individuals looking for a product with minimal yet beneficial ingredients.

BRIEF DESCRIPTION OF THE DRAWINGS

FIG. 1 is a table illustrating the nutritional make-up of the treatment composition and the placebo.

DETAILED DESCRIPTION OF THE INVENTION

The present invention is based, at least in part, on the unexpected discovery that high flavanol cocoa when combined with a number of other protein components exhibit synergistic health benefits, including, but not limited to, enhancing both mental and physical performance during athletic activity.

When a high flavanol (for example, but not limited to, Diosmin, Myricetin, Isoquercetin, Eriocitrin, and Narirutin) cocoa powder is consumed with a refined protein powder such as, but not limited to, whey, whey protein isolate, egg albumin protein and/or a vegetable based protein such as, for example, peanut, soy, pea, hemp, brown rice, etc., it has been found that an increase in nutrient availability is achieved. Among other various benefits, this increase in nutrient availability helps speed muscle recovery and repair time. This shortening of time reduces the time an athlete needs to recover before returning to training.

As used herein, the definition of high flavanol cocoa is defined as a cocoa containing at least 2.0% of its weight in flavonoids, and in a preferred form at least 3.75% of its weight in flavonoids, and in a further preferred form containing at least 4.0% of its weight in flavonoids, and in still a further preferred form containing at least 7.5% of its weight in flavonoids, and in an even further preferred form containing at least 12% of its weight in flavonoids. It is contemplated that a minimum serving consists of 2.5 grams of cocoa containing at least 100 mg of flavanols, and in a preferred form containing at least a minimum serving consists of 5 grams of cocoa containing at least 187.5 mg of flavanol, and in a further preferred form containing at least 200 mg of flavanol, and in still a further preferred form containing at least 375 mg of flavanol, and in an even further preferred form containing at least 400 mg of flavanols, and in yet even a further preferred form containing at least 2,200 mg of flavanols. This minimum flavanol serving is preferably combined with a minimum of 2 grams of protein, and in a preferred form containing at least 6 grams of protein, and in a further preferred form containing at least 12 grams of protein, and in an even further preferred form containing at least 48 grams of protein. Preferably, the protein is a refined whey protein isolate. Of course, as noted above, other proteins are contemplated. Additionally, the protein component may be provided in the form of powdered milk.

The inventive composition may be administered in a number of forms, including but not limited to, powder, liquid, bar, cookie, waffle, syrup, tablet and/or dietary supplement. As a powder, it may be mixed with a liquid, such as, for example, water, juice or milk, or may be sprinkled on a food product. As a liquid, it may be directly consumed or mixed with another liquid. Similarly, as a syrup, it may be directly consumed, mixed with another liquid, or applied to a food product. Additional ingredients, such as binders, etc. may be added to form the composition into a solid consumable, such as, for example, a bar, cookie or waffle. Additionally, the composition may be reduced to a tablet and ingested in tablet form. Further, the form of the composition for administering to a mammal is not limited to those forms set forth herein, and the inventive composition may take a myriad forms without departing from the spirit and scope of the present invention.

As shown and illustrated below in the various studies and testing, a preferred mixture of cocoa flavanols with protein shows a greater benefit achievably for athletic performance beyond each individual component in an unexpected synergistic manner. The inventive composition has been found to provide a synergistic increase in athletic performance, both physical as well as mental, during physical activity when consumed before, during, and/or after physical activity, as well as daily as a dietary supplement.

Example 1—Cycling Testing

Study Participants:

Eleven (11) Study Participants were selected from male and female cyclists, ranging in various above average abilities in cycling skills with a minimum of 18 months of cycling experience and various ages ranging from 24 years of age to 46 years of age.

Study Design:

Study Participants were randomized in a Placebo controlled design study. Some Participants received the Placebo and some received the Treatment including the inventive composition. None of the Participants were told whether they were receiving the Placebo or the Treatment.

Products Design and Administration:

Both the Placebo and the Treatment used the same amount of protein and the same amount of sugar. The protein was 16 grams of a dried milk powder, which resulted in 5.76 grams of protein being delivered. The sugar used was 5 grams of cane sugar. The Treatment and Placebo used 2.67 g of Cocoa. The Treatment used Cocoa Elite's unsweetened cocoa with a 7.5% flavanol content or roughly 200 mg of flavanols. The Placebo contained a cocoa powder processed with alkali, with a flavanol content of roughly 1% or 26 mg of flavanol. The Treatment and Placebo were packaged in identical pouches. The detailed nutritional breakdown is shown in FIG. 1.

Additionally, a fourteen (14) day supply of cocoa was provided to the Study Participants in identical canisters of similar makeup. This product was used for the loading stage of the test. The cocoa flavanol for the Treatment group delivered 400 mg of Flavanols per serving, while the cocoa flavanol for the Placebo group delivered 53 mg of flavanols.

Equipment:

Various cycling power meters and bicycles were used to facilitate the testing. Each Study Participant self-administered the test using their own equipment.

Testing Procedure:

The Treatment mixture versus Placebo mixture was randomly assigned. None of the Study Participants knew which one they were receiving. The Placebo mixture was designed to look, smell, and taste like the Treatment mixture. The Study Participants were asked not to consume cocoa or chocolate throughout the test period, other than the test product provided for the test period. The Study Participants were also asked to refrain from using any cocoa or chocolate product for the 5 days before starting the test.

Each Study Participant completed an Adapted Field Test Protocol consisting of a warm-up; fast pedals; 5-minute all-out; 12-minute recovery; 8-minute Threshold effort; 8-minute recovery; 8-minute Threshold effort; and 10-minute cool down.

At the completion of the test protocol, the Study Participants were asked to complete a Numerical Rating Scale ("NRS") used to assess athletic performance on 12 variables (concentration, exhaustion, alertness, pep, worn out, performance accuracy, focus, stamina, overall energy, mental energy, physical energy, and consistency) was administered at the completion.

During the next 14 days, the Study Participants were instructed to consume the cocoa powder every day during their breakfast, from the canister containing the cocoa powder.

After 14 days, the Study Participants repeated the above Adapted Field Test Protocol. At the conclusion of the test protocol, the Study Participants drank either the Treatment or the Placebo product in 8 oz. of water. After the Study Participants consumed the product, they completed a second NRS using the same criteria as above.

The Study Participants then rested for approximately 1 hour, and then completed the following RAMP Protocol: a 15-minute warm-up, fast pedals for 3 minutes, then a ramp protocol starting at their tempo power and increasing by 10 watts every 2 minutes until failure/fatigue. A final NRS assessment was completed.

Data Analysis:

A multiple measurement using a statistical method of making simultaneous comparison using analysis of variance is employed to examine the differences between the Placebo mixture and the Treatment mixture. The data was analyzed using Microsoft Excel and an ANOVA: Single Factor, as well as t-Test: Two-Sample Assuming Equal Variances and t-Test: Two-Sample Assuming Unequal Variances.

The numbers representing responses of the Study Participant are provided below in Table B1. The scores were averaged, with each score being from 1 to 100 for each variable at the completion of the RAMP Protocol. The higher the score, the more positive the response noted by the Study Participant.

TABLE B1

Comparison of Athletic Performance between Treatment and Placebo using NRS after the Cycling RAMP Protocol.
Average Score after completing Ramp Protocol

|  | Treatment | Placebo |  |
| --- | --- | --- | --- |
| Concentration | 85.8 | 69.8 |  |
| Exhaustion | 39.2 | 11.8 | ** |
| Alertness | 80.8 | 77.0 |  |
| Pep | 72.0 | 58.0 |  |
| Worn out | 45.0 | 14.0 | ** |
| Performance Accuracy | 75.8 | 56.6 |  |
| Focus | 80.0 | 65.0 |  |
| Stamina | 80.3 | 56.0 | ** |
| Energy | 79.2 | 59.8 |  |
| Mental Energy | 73.3 | 72.0 |  |
| Physical Energy | 71.7 | 55.6 |  |
| Consistency | 71.5 | 69.0 |  |

** Statistically significant at .05 level

Results:

With comparison to Placebo, the Treatment had a statistically significant positive effect on the criteria of Worn Out, Stamina, and Exhaustion, out of the 12 variables recorded. Although not statistically significant with comparison of the Placebo, the Treatment had a positive impact on all of the remaining variables: Concentration, Pep, Alertness, Performance Accuracy, Focus, Energy, Mental Energy, Physical Energy and Consistency. Thus, the Treatment provided an increase in each of the 12 criteria analyzed related to athletic performance.

Additionally, as shown in Table B2 below, the average values of all 12 criteria variables related to athletic performance show a statistically significant improvement when the Treatment is compared against the Placebo.

TABLE B2

ANOVA Analysis comparing the averages of the NRS for Cycling Test.
Anova: Single Factor

SUMMARY

| Groups | Count | Sum | Average | Variance |
| --- | --- | --- | --- | --- |
| Treatment | 12 | 854.6666667 | 71.22222222 | 206.4360269 |
| Placebo | 12 | 664.6 | 55.38333333 | 442.679697 |

ANOVA

| Source of Variation | SS | df | MS | F | P-value | F crit |
| --- | --- | --- | --- | --- | --- | --- |
| Between Groups | 1505.222407 | 1 | 1505.222407 | 4.637762889 | 4.25% | 4.300949502 |
| Within Groups | 7140.272963 | 22 | 324.557862 |  |  |  |
| Total | 8645.49537 | 23 |  |  |  |  |

Conclusion:

The flavanol cocoa when combined with a protein enhances athletic performance by providing a statistically significant increase in attributes related to physical performance, but also increasing the perceived mental state on performance which provides an additional increase in overall athletic performance.

Example 2—Treadmill Testing

Study Participants:

Seven (7) Study Participants were selected from male and female runners ranging in various abilities from running a minimum of 6 miles per week to 80 miles per week and various ages ranging from 27 years of age to 49 years of age.

Study Design:

Study Participants were randomized in a crossover placebo controlled design. Some Participants received the Placebo and some received the Treatment including the inventive composition. None of the Participants were told whether they were receiving the Placebo or the Treatment.

Products Design and Administration:

Both the Placebo and the Treatment used the same amount of protein and the same amount of sugar. The protein was 32 grams of a dried milk powder, which resulted in 11.52 grams of protein being delivered. The sugar used was 10 grams of cane sugar. The Treatment and Placebo used 5.334 g of Cocoa. The Treatment used Cocoa Elite's unsweetened cocoa with a 7.5% flavanol content or roughly 400 mg of flavanols. The Placebo contained a cocoa powder processed with alkali, with a flavanol content of roughly 1% or 53 mg of flavanol. The Treatment and Placebo were packaged in identical pouches. The detailed nutritional breakdown is shown in FIG. 1. One of the Study Participants was allergic to lactose. Consequently, this Study Participant's Treatment mixture and Placebo mixture were formulated with equal amounts of protein and carbohydrates based on a vegetable composition. The cocoa used for this Study Participant was formulated as indicated above, thus preserving the testing protocol to study only the effects of cocoa flavanols. It also highlights that various other forms of proteins, carbohydrates and fats can be combined for the benefit of athletic performances, as indicated within the present invention.

Equipment:

A standard treadmill with incline capability was used for testing. Each Study Participant was instructed to use the same make and model treadmill for their individual tests. An independent personal trainer was generally present to record the results and monitor the activities for both tests.

Testing Procedure:

The treatment mixture versus placebo mixture was randomly assigned. None of the Study Participants knew which one they were receiving. The Placebo mixture was designed to look, smell, and taste like the Treatment mixture. The Study Participants were asked not to consume cocoa or chocolate throughout the test period, as well as the 5 days before the testing began. Each Study Participant was asked to run on the treadmill for 20 minutes to fatigue the body. The speed and incline were recorded for repeat use during the crossover test. After the 20 minutes, the Study Participants were given either the Placebo or Treatment mixture to consume. After a 20-minute rest the Study Participant completed a ramp protocol with a set incline of 2% and a starting speed of 4 MPH. Every 2 minutes the speed was increased by ½ MPH until the Study Participant could not continue (e.g., to failure). Heart rate, speed and duration were recorded.

A Numerical Rating Scale ("NRS") used to assess athletic performance on 12 variables (concentration, exhaustion, alertness, pep, worn out, performance accuracy, focus, stamina, overall energy, mental energy, physical energy, consistency) was administered at the completion.

After five days, the Study Participants returned and completed the crossover test using the other product. By crossover test is meant that the Study Participants redid the exact same treadmill test, but consumed the other product. Those who consumed the Treatment the first time, consumed the Placebo the second time. Those who consumed the Placebo the first time, consumed the Treatment the second time. None of the Study Participants knew what product they were consuming either time.

Data Analysis:

A multiple measurement using a statistical method of making simultaneous comparison using analysis of variance is employed to examine the differences between the Placebo mixture and the Treatment mixture. The data was analyzed using Microsoft Excel and an ANOVA: Single Factor, as well as t-Test: Two-Sample Assuming Equal Variances and t-Test: Two-Sample Assuming Unequal Variances.

The Study Participants ran for a total of 142.25 minutes covering a distance of 90,906 feet after consuming the Placebo mixture. The Study Participants ran for a total of 150.951 minutes covering a distance of 102,408 feet after consuming the Treatment mixture.

The numbers representing responses of the Study Participant are provided in Table 1 below. The scores were averaged, with each score being from 1 to 100 for each variable. The higher the score, the more positive the response noted by the Study Participant.

TABLE 1

Comparison of Athletic Performance between Treatment and Placebo using NRS for Treadmill Test.

|  | Treatment Mixture | Placebo Mixture |
|---|---|---|
| Concentration | 87.14 | 80.71 |
| Exhaustion | 74.29 ** | 36.43 ** |
| Alertness | 87.14 | 77.86 |
| Pep | 61.14 | 58.57 |
| Worn out | 59.29 | 30.71 |
| Performance Accuracy | 91.67 | 90.83 |
| Focus | 80.00 | 68.57 |
| Stamina | 68.57 | 54.29 |
| Energy | 65.00 ** | 34.29 ** |
| Mental Energy | 75.71 | 57.86 |
| Physical Energy | 67.14 ** | 34.29 ** |
| Consistency | 83.33 | 80.00 |

** Statistically significant at .05 level

Results:

The increase of 8.7 minutes in time-before-complete-failure represents an average increase of 6.12% using the Treatment when compared against the Placebo. The increase in distance ran of 11,502 feet, represents a 12.7% improvement using the Treatment when compared against the Placebo. Although these amounts are not statistically significant at $P<0.005$, they do show that there is a positive impact of the Treatment when compared to the Placebo in both total distance travelled and total time before exhaustion.

With comparison to Placebo, the Treatment had a statistically significant positive effect on the criteria of Physical Energy, Energy, and Exhaustion, out of the 12 variables recorded. Although not statistically significant with comparison of the Placebo, the Treatment had a positive impact on all the remaining variables: Concentration, Pep, Alertness, Worn Out, Performance Accuracy, Focus, Stamina, Mental Energy and Consistency. Thus, the Treatment provided an increase in each of the 12 criteria analyzed related to athletic performance.

Additionally, as shown in Table 2 below, the average values of all 12 variables related to athletic performance show a statistically significant improvement when the Treatment is compared against the Placebo.

TABLE 2

ANOVA Analysis of NRS Scores for Treadmill Test.
Anova: Single Factor

SUMMARY

| Groups | Count | Sum | Average | Variance |
|---|---|---|---|---|
| Treatment Mixture | 12 | 900.4285714 | 75.03571429 | 119.1041538 |
| Placebo Mixture | 12 | 704.4047619 | 58.70039683 | 447.895945 |

ANOVA

| Source of Variation | SS | df | MS | F | P-value | F crit |
|---|---|---|---|---|---|---|
| Between Groups | 1601.055579 | 1 | 1601.055579 | 5.647461377 | 2.66% | 4.300949502 |
| Within Groups | 6237.001087 | 22 | 283.5000494 |  |  |  |
| Total | 7838.056666 | 23 |  |  |  |  |

Conclusion:

The flavanol cocoa when combined with a protein enhances athletic performance by increasing the perceived mental state on performance and there is an increase in time-to-complete-failure improvement as well as distanced travel. This represents an improvement in endurance. There is also a gain in fatigue recovery and athletic recovery, as well as a general increase in overall athletic activity. Furthermore, the increase in oxygen consumption can be concluded based on the increase in time-to-complete-failure improvement.

Example 3—Weight-Strength Training Testing

Study Participants:

Seven (7) Study Participants were selected from male and female weight-strength training individuals ranging in abilities and ages ranging from 26 years of age to 53 years of age. The Study Participants currently have been participating in weight-strength training for a minimum of 5 years of experience and not greater than 15 years of experience.

Study Design:

Study Participants randomized in a crossover placebo controlled design. Some Participants received the Placebo and some received the Treatment including the inventive composition. None of the Participants were told whether they were receiving the Placebo or the Treatment.

Products Design and Administration:

Both the Placebo and the Treatment used the same amount of protein and the same amount of sugar. The protein was 32 grams of a dried milk powder, which resulted in 11.5 grams of protein being delivered. The sugar used was 10 grams of cane sugar. The Treatment and Placebo used 5.34 g of Cocoa. The Treatment used Cocoa Elite's unsweetened cocoa with a 7.5% flavanol content or roughly 400 mg of flavanols. The Placebo contained a cocoa powder processed with alkali, with a flavanol content of roughly 1% or 53 mg of flavanol. The Treatment and Placebo were packaged in identical pouches. The detailed nutritional breakdown is shown in FIG. 1.

Equipment:

Various equipment was used to facilitate the implementation of the testing procedures used. Since this was a crossover study to measure the effect of cocoa flavanol and protein on various activity, flexibility was granted in which equipment could be used. Some Study Participants used free weights and others used machines. However, each Study Participant used the same equipment (whether free weights or machines) for the initial and the crossover test to ensure the same equipment was used for both the Treatment and the Placebo. An independent personal trainer was present to record the results and monitor the activities for both tests.

Testing Procedure:

The Treatment mixture versus Placebo mixture was randomly assigned. The Placebo mixture was designed to look, smell, and taste like the Treatment mixture. The Study Participants were asked to not consume cocoa or chocolate throughout the test period, other than the test product provided for the test period, as well as the 5 days before the testing began.

Each Study Participant performed the following exercises and recorded the weight used and number of repetitions or elapsed:

Squats—using ½ their body weight complete repetition until failure.

Push-ups—repetitions until failure.

Planks—timed from start of exercise until failure (i.e., how long can Study Participant hold the plank position).

Shoulder press—using a personally selected weight complete repetition until failure.

Leg Press—using ½ body weight complete repetition until failure.

Bicep curl—using a personally selected weight complete repetition until failure.

After completing the above exercises, the Study Participant drank a randomly assigned product containing either the Placebo or the Treatment.

A Numerical Rating Scale ("NRS") used to assess athletic performance on 11 variables (concentration, focus, exhaustion, stamina, pep, worn out, physical energy, mental energy, performance accuracy, consistency and energy) was administered at the completion of the exercises.

Then, the Study Participants rested for 30 minutes. Each Study Participant then completed the exercises a second time, recording the weight used and number of repetitions or elapsed time, as well as a NRS assessment of the 11 variables.

After five days the Study Participants returned and completed the crossover test using the other product. By crossover test is meant that the Study Participants redid the exact same weight-strength training test, but consumed the other product. Those who consumed the Treatment the first time, consumed the Placebo the second time. Those who consumed the Placebo the first time, consumed the Treatment the second time. None of the Study Participants knew what product they were consuming either time.

Data Analysis:

A multiple measurement using a statistical method of making simultaneous comparison using analysis of variance is employed to examine the differences between the Placebo mixture and the Treatment mixture. The data was analyzed using Microsoft Excel and an ANOVA: Single Factor.

The numbers representing responses of the Study Participants are provided in Table W1 below. The scores were averaged, with each score being from 1 to 100 for each variable. The higher the score, the more positive the response noted by the Study Participant.

TABLE W1

Comparison of Athletic Performance between Treatment and Placebo using NRS for Weight-Strength Training Test.

| | Treatment | Placebo | |
|---|---|---|---|
| Concentration | 89.3 | 77.1 | |
| Focus | 87.6 | 73.6 | |
| Exhaustion | 74.3 | 57.9 | |
| Stamina | 82.4 | 58.6 | ** |
| Pep | 82.6 | 67.1 | |
| Worn out | 73.6 | 61.4 | |
| Physical Energy | 80.7 | 60.7 | |
| Mental Energy | 84.3 | 72.1 | |
| Performance Accuracy | 87.1 | 80.0 | |
| Consistency | 86.6 | 75.9 | |
| Energy | 84.7 | 61.4 | ** |

** Statistically significant at .05 level

Results:

The Treatment had a positive effect in total number of repetitions or a positive increase in time as show in Table W2. All exercises showed improvement in the quantity of repetitions or an improvement in time when the Treatment mixture was compared to the Placebo mixture.

TABLE W2

Increase in repetitions or time the Treatment had over the Placebo. Treatment compared to Placebo

|  | Total Increase | Average Increase | % increase | |
|---|---|---|---|---|
| Squats | 93.00 | 13.29 | 19.75% | Repetition |
| Push ups | 33.00 | 4.71 | 18.03% | Repetition |
| Plank Time | 64.43 | 9.20 | 12.63% | Seconds |
| Shoulder Press | 15.00 | 2.14 | 9.15% | Repetition |
| Leg Press | 114.00 | 16.29 | 18.84% | Repetition |
| Bicep Curls | 41.00 | 5.86 | 20.10% | Repetition |

With comparison to Placebo, the Treatment had a statistically significant positive effect on the criteria of Stamina and Energy out of the 11 variables recorded.

Although not statistically significant with comparison of the Placebo, the Treatment had a positive impact on all remaining variables related to athletic performance: Concentration, Focus, Exhaustion, Pep, Worn Out, Physical Energy, Mental Energy Performance Accuracy, and Consistency.

Additionally, as shown in Table 3 below, the average values of all 11 variable show a statistically significant improvement when the Treatment is compared against the Placebo, P-value <0.01.

TABLE 3

ANOVA Analysis of NRS Scores for Weight-Strength Training Test.
Anova: Single Factor

SUMMARY

| Groups | Count | Sum | Average | Variance | | |
|---|---|---|---|---|---|---|
| Treatment | 11 | 913.1428571 | 83.01298701 | 26.54879406 | | |
| Placebo | 11 | 745.8571429 | 67.80519481 | 66.90723562 | | |

ANOVA

| Source of Variation | SS | df | MS | F | P-value | F crit |
|---|---|---|---|---|---|---|
| Between Groups | 1272.023 | 1 | 1272.023191 | 27.22185386 | 0.0042% | 4.351243503 |
| Within Groups | 934.5603 | 20 | 46.72801484 | | | |
| Total | 2206.583 | 21 | | | | |

Conclusion:

The flavanol cocoa when combined with a protein enhances athletic performance by increasing the perceived mental state on performance and there is an increase in either repetitions or time before exhaustion. The gains in repetitions and time before exhaustion highlight the gain in endurance as well as strength. There is also evidence to support fatigue recovery and athletic recovery, as well a general increase in athletic performance.

Most endurance and recovery products used by athletes range from a low ratio of approximately 1:1 (carbohydrates to protein) to a high a ratio of approximately 5.5:1 (carbohydrates to protein). The addition of cocoa flavanols to any product within these ratios will provide the added benefit which the present invention has shown is possible with the addition of cocoa flavanols to a product meant to be consumed for athletic performance. Since previous art and science has already shown that endurance and recovery are affected within those ranges, testing all variations of different ratios would be redundant. Furthermore, previous art and science has shown that consumption of endurance and recovery products of varying ratios has very little impact on athletic performance beyond the ranges shown above. Consequently, the present invention shows that adding cocoa flavanols to products consumed by athletic-minded individuals has an overall benefit as defined within the present invention. Furthermore, athletes and sports-oriented individuals looking for a natural and a minimal number of ingredients within a product, would benefit from the present invention which might only contain three ingredients such as, for example, powdered milk, high flavanol cocoa powder, and cane sugar.

The inventive product composition could be made with a cocoa powder which has cocoa flavanol in the range of 2% to 28% by weight. Any additional flavanols beyond 2,200 mg will cause the product composition to become too bitter, too thick or require too much liquid which would need to be consumed.

The present invention can also be carried out in a plurality of modifications of the examples shown herein and of aspects of the present invention that are pointed out above.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

What is claimed is:

1. A composition for consumption before, during and/or after physical activity for improving one or more of overall strength in a mammal, fatigue recovery in a mammal, athletic recovery in a mammal, increased endurance in a mammal, and overall athletic performance in a mammal, the composition comprising:
   1 to 21.32 grams of cocoa powder;
   1 to 48 grams of protein;
   0 to 193 grams of carbohydrate; and
   0 to 24 grams of fat to the mammal, and
   wherein the cocoa powder contains at least 7.5% of its weight in flavonoids.

2. The composition of claim 1, wherein the composition is selected from a powder, liquid, bar, cookie, waffle, syrup, tablet or dietary supplement.

3. The composition of claim 1, wherein the cocoa powder comprises 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

4. The composition of claim 1, wherein various vitamins, minerals, flavoring agents or sweeteners are added to the composition to enhance flavor.

5. The composition of claim 1, wherein the mammal is human.

6. The composition of claim 1, wherein the protein is animal based or plant based or chemically formulated.

7. A method of improving overall athletic performance in a mammal in need of or having a desire to improve their overall athletic performance, the method comprising:
   administering a preparation comprising: 1 to 21.32 grams of cocoa powder; 1 to 48 grams of protein; 0 to 193 grams of carbohydrate; and 0 to 24 grams of fat to the mammal, thereby resulting in said mammal having improvement in their overall athletic performance,
   wherein the preparation comprises a composition selected from a powder, liquid, bar, cookie, waffle, syrup, tablet or dietary supplement, and
   wherein the cocoa powder contains at least 7.5% of its weight in flavonoids.

8. The method of claim 7, wherein the cocoa powder comprises 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

9. The method of claim 7, wherein various vitamins, minerals, flavoring agents or sweeteners are added to the composition to enhance flavor.

10. The method of claim 7, wherein the mammal is human.

11. The method of claim 7, wherein the protein is animal based or plant based or chemically formulated.

12. The method of claim 7, wherein the mammal is in need of increasing endurance.

13. The method of claim 7, wherein the mammal is in need of athletic recovery.

14. The method of claim 7, wherein the mammal is in need of fatigue recovery.

15. The method of claim 7, wherein the mammal is in need of improving overall strength.

16. A method of improving increased endurance in a mammal in need of or having a desire to improve their increased endurance, the method comprising:
   administering a preparation comprising: 1 to 21.32 grams of cocoa powder; 1 to 48 grams of protein; 0 to 193 grams of carbohydrate; and 0 to 24 grams of fat to the mammal, thereby resulting in said mammal having improvement in their increased endurance,
   wherein the preparation comprises a composition selected from a powder, liquid, bar, cookie, waffle, syrup, tablet or dietary supplement, and
   wherein the cocoa powder contains at least 7.5% of its weight in flavonoids.

17. The method of claim 16, wherein the cocoa powder comprises 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

18. The method of claim 16, wherein various vitamins, minerals flavoring agents or sweeteners are added to the composition to enhance flavor.

19. The method of claim 16, wherein the mammal is human.

20. The method of claim 16, wherein the protein is animal based or plant based or chemically formulated.

21. A method of improving athletic recovery in a mammal in need of or having a desire to improve their athletic recovery, the method comprising:
   administering a preparation comprising: 1 to 21.32 grams of cocoa powder; 1 to 48 grams of protein; 1 to 148 grams of carbohydrate; and 1 to 24 grams of fat to the mammal, thereby resulting in said mammal having improvement in their athletic recover,
   wherein the preparation comprises a composition selected from a powder, liquid, bar, cookie, waffle, syrup, tablet or dietary supplement, and
   wherein the cocoa powder contains at least 7.5% of its weight in flavonoids.

22. The method of claim 21, wherein the cocoa powder comprises 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

23. The method of claim 21, wherein various vitamins, minerals, flavoring agents or sweeteners are added to the composition to enhance flavor.

24. The method of claim 21, wherein the mammal is human.

25. The method of claim 21, wherein the protein is animal based or plant based or chemically formulated.

26. A method of improving fatigue recovery in a mammal in need of or having a desire to improve their fatigue recovery, the method comprising:
   administering a preparation comprising: 1 to 21.32 grams of cocoa powder; 1 to 48 grams of protein; 1 to 148 grams of carbohydrate; and 1 to 24 grams of fat to the mammal, thereby resulting in said mammal having improvement in their fatigue recovery,
   wherein the preparation comprises a composition selected from a powder, liquid, bar, cookie, waffle, syrup, tablet or dietary supplement, and
   wherein the cocoa powder contains at least 7.5% of its weight in flavonoids.

27. The method of claim 26, wherein the cocoa powder comprises 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

28. The method of claim 26, wherein various vitamins, minerals, flavoring agents or sweeteners are added to the composition to enhance flavor.

29. The method of claim 26, wherein the mammal is human.

30. The method of claim 26, wherein the protein is animal based or plant based or chemically formulated.

31. A method of improving overall strength in a mammal in need of or having a desire to improve their overall strength comprising:
   administering a preparation comprising: 1 to 21.32 grams of cocoa powder; 1 to 48 grams of protein; 1 to 148 grams of carbohydrate; and 1 to 24 grams of fat to the mammal, thereby resulting in said mammal having improvement in their overall strength,
   wherein the preparation comprises a composition selected from a powder, liquid, bar, cookie, waffle, syrup, tablet or dietary supplement, and
   wherein the cocoa powder contains at least 7.5% of its weight in flavonoids.

32. The method of claim 31, wherein the cocoa powder comprises 100 to 2,200 mg of cocoa flavanol containing at least one of the derivatives of catechin, (−)-epicatechin, epicatechin gallate, epigallocatechin, epigallocatechin gallate, proanthocyanidins, theaflavins, and thearubigins.

33. The method of claim 31, wherein various vitamins, minerals, flavoring agents or sweeteners are added to the composition to enhance flavor.

34. The method of claim 31, wherein the mammal is human.

35. The method of claim 31, wherein the protein is animal based or plant based or chemically formulated.

* * * * *